(12) United States Patent
Zhi et al.

(10) Patent No.: US 11,664,500 B2
(45) Date of Patent: May 30, 2023

(54) CATHODE MATERIAL

(71) Applicant: City University of Hong Kong, Kowloon (HK)

(72) Inventors: Chunyi Zhi, Kowloon (HK); Xinliang Li, Kowloon (HK); Zhaodong Huang, Kowloon (HK); Ze Chen, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 11 days.

(21) Appl. No.: 17/339,926

(22) Filed: Jun. 4, 2021

(65) Prior Publication Data
US 2022/0393172 A1  Dec. 8, 2022

(51) Int. Cl.
| | | |
|---|---|---|
| *H01M 12/08* | (2006.01) | |
| *H01M 10/36* | (2010.01) | |
| *H01M 4/60* | (2006.01) | |
| *C07C 211/09* | (2006.01) | |
| *H01M 4/02* | (2006.01) | |

(52) U.S. Cl.
CPC ............. *H01M 4/60* (2013.01); *C07C 211/09* (2013.01); *H01M 10/365* (2013.01); *H01M 2004/028* (2013.01)

(58) Field of Classification Search
CPC ................ H01M 4/60; H01M 10/365; H01M 2004/028; H01M 12/085; H01M 4/244; C07C 211/09
See application file for complete search history.

(56) References Cited

PUBLICATIONS

Cesium Lead Bromide Perovskite-Based Lithium-Oxygen Batteries, Zhou et al., Nano Letters 2021 21 (11), 4861-4867.*
Surface mediated ligands addressing bottleneck of room-temperature synthesized inorganic perovskite nanocrystals toward efficient light-emitting diodes, J. Dai et al, Nano Energy 70 (2020) 104467.*
Efficient and Stable Perovskite Solar Cell with High Open-Circuit Voltage by Dimensional Interface Modification, Luo et al, ACS Applied Materials & Interfaces 2019 11 (9), 9149-9155.*
Defect Passivation of Organic-Inorganic Hybrid Perovskites by Diammonium Iodide toward High-Performance Photovoltaic Devices, Zhao et al, ACS Energy Lett. 2016, 1, 757-763.*

* cited by examiner

*Primary Examiner* — Haidung D Nguyen

(57) ABSTRACT

The present invention relates to a range of halide organic salts and their use in a cathode of an electrical cell and in batteries. Elemental halides have attracted intense interest as promising electrodes for energy storage. However, they suffer from a number of inherent physicochemical drawbacks, including the volatility of iodine, the corrosiveness of liquid bromine. The salts of the present invention may serve as a cathode matched with a zinc anode avoiding these issues.

3 Claims, 14 Drawing Sheets

CATHODE MATERIAL

This invention relates to a halide organic salt particularly but not exclusively for use as a cathode in an electronic storage device, such as an aqueous zinc battery. The present invention also relates to a cathode and battery comprising the salt of the present invention.

BACKGROUND

Elemental halides have attracted intense interest as promising electrodes for energy storage. However, they suffer from a number of inherent physicochemical drawbacks, including the volatility of iodine, the corrosiveness of liquid bromine, the undesired loss of halide material from the electrode during charging and discharging cycles, and the low electron shuttle efficiency between a conductor and the halide material.

In the field of safe energy storage, aqueous rechargeable zinc-ion batteries have been contemplated on account of their inherent non-toxicity, low cost, high specific capacity (820 mAh $g^{-1}$), and low redox potential (−0.76 V vs. SHE). Among the numerous available cathode candidates, conversion-type halides (—Br, —I) have become one of the most competitive sources due to their high redox potentials and capacities. Ideally, the redox potential of I is 0.62 V vs. SHE, with a theoretical capacity of 211 mAh $g^{-1}$ and corresponding to the redox process: $2I^- - 2e^- \rightarrow I_2$. As for Br, the redox potential is 1.08 V and the theoretical capacity is 350 mAh $g^{-1}$ following redox process: $2Br^- - 2e^- \rightarrow Br_2$. Paired with a Zn anode ($Zn - 2e^- \rightarrow Zn^{2+}$), the ideal output plateaus for $Br_2$ and $I_2$ can reach up to 1.84 V and 1.38 V, respectively, exceeding other widely studied cathodes (0.4-1.1 V for V-oxides, 1.0-1.6 V for Mn-oxides, 0.7-1.2 V for polymers) in aqueous electrolytes.

However, many intrinsic drawbacks have hindered their further development. Firstly, the physicochemical properties of the elemental active materials are problematic. Although elemental $I_2$ is a solid it has a high vapor pressure causing it to have a high rate of sublimation even at ambient conditions. This in turn results in undesired instability and leakage. Elemental $Br_2$ exists in a liquid state and is extremely corrosive. Furthermore, both elements are poor conductors. Consequently, the redox reactions required for current flow must rely on external conductive carriers to support the halide and supply electrons. The resultant electron shuttle efficiency between the conductive host and the non-conductive halide guest determines the whole conversion kinetics of the redox reaction (the redox kinetics). As such, in certain embodiments, it is an object of the present invention to provide improved redox kinetics.

Furthermore, iodine conversion involves a solid-liquid reaction. The intermediate product, polyiodide (mainly $I_3^-$), leads to undesired leakage of the active materials associated with capacity deterioration as the number of charge/discharge cycles increases. This negative effect is further amplified for the bromine system since the redox reaction concerns a liquid-liquid mechanism. Accordingly, an object of certain embodiments of the present invention is to avoid loss of halide species during the charging and discharging processes.

A further problem, particularly in aqueous media is that the highly soluble polyhalides require stricter requirements on the conductive host. For iodine electrodes, traditional porous materials such as active carbon, graphene, ZIF, and MOF have been employed as the host through simple physical adsorption, chemical vapor deposition (CVD), or an impregnation process. As a result of the poor host-guest interaction between prior art halides and investigated hosts, the cycle lifespan of $Zn-I_2$ batteries has started to falter in the range of 5000 cycles. Further, the use of bromine presents unique problems associated with bromine being a liquid. There is also a limited number of available hosts for stationary $Zn-Br_2$ batteries. Additionally, an object of certain embodiments of the present invention is to improve the confinement of a halide within a host species.

U.S. Pat. No. 8,343,661 discloses a cathode composition comprising, (i) particles comprising a transition metal selected from the group consisting of Ni, Fe, Cr, Mn, Co, V, and combinations thereof; (ii) alkali halometallate; (iii) alkali halide; (iv) one or more source of Zn; and (v) one or more sources of chalcogenide.

BRIEF SUMMARY OF THE DISCLOSURE

In a first aspect, the invention proposes a salt comprising a host and guest pair for use as an electrode, wherein the host is a protonated hydrocarbon; the guest is a halogen; the protonated hydrocarbon capable of binding to the halogen in the different valence states of the halogen required for the operation of the electrode.

As the skilled reader would know, host-guest chemistry is a branch of supramolecular chemistry that describes complexes that are composed of two or more molecules or ions that are held together in unique structural relationships by forces other than those of full covalent bonds. These non-covalent bondings include ionic bonding, hydrogen bonds, van de Waals forces, hydrophobic interactions. These relationships are often in a state of thermodynamic equilibrium between the unbound state and the bound state. The host component is usually the larger molecule, and it encompasses the smaller guest molecule.

Preferably, the protonated hydrocarbon comprises an amine group; the molecule weight of the hydrocarbon being such that the halogen is physically retained as part of the electrode in all the different valence states of the halogen required for the operation of the electrode.

Other organic functional groups capable of binding to the halogen in the different valence states of the halogen required for the operation of the electrode is within contemplation of this application. Furthermore, in some embodiments only one such amine group or functional group is present for interacting with the halogen. In other embodiments, the hydrocarbon is a molecular chain having two ends, and one functional group is present at each end. The functional groups at the two ends may be the same or different. Yet in other embodiments, a branched hydrocarbon molecule having three or more functional groups is possible.

Typically, the halogen is bromine or iodine.

Therefore, the invention provides a possibility of improving confinement of the halide in a halide-based cathode, by improving the host-guest affinity leading to suppression of leakage of the halide. This mitigates the instability and safety hazards of the elemental halide.

The present invention provides a salt for use as an electrode in an energy storage device, wherein the salt is formed of an acid, selected from HBr, HI or a combination thereof, and an amine, the salt having dissociated bromine ions and/or iodine ions, wherein the amine is a hydrocarbon amine having a hydrocarbon structure that allows for retention of bromine ions and/or iodine ions and also allows electron transfer.

In certain embodiments the salt is a crystalline material.

In certain embodiments the amine comprises at least two amine groups, wherein the amine groups are protonated by the acid.

In certain embodiments the hydrocarbon amine is a non-cyclic hydrocarbon.

In certain embodiments the hydrocarbon amine is an alkylamine or an alkenylamine.

In an embodiment of the invention there is provided a salt for use as an electrode in an energy storage device, wherein the salt is formed of an amine selected from: $C_{4-20}$ alkylamine, $C_{4-20}$ alkyldiamine, $C_{4-20}$ alkenylamine, or $C_{4-20}$ alkenyldiamine; and an acid selected from HBr, HI or a combination thereof. Without being bound by theory, it is believed that the alkyl or alkenyl chain can act as a framework within which bromine and/or iodine ions (referred to herein as halide ions) are hosted. Where the alkyl and alkenyl chains have a strong host-guest interaction with the halides ions, retaining the halide ions within the carbon framework. This in turn reduces loss of the halide ions during the redox reactions occurring during charging and discharging of an electrochemical cell.

In an embodiment the amine is selected from: $C_{6-12}$ alkylamine, $C_{6-12}$ alkyldiamine, $C_{6-12}$ alkenylamine, and $C_{6-12}$ alkenyldiamine. In an embodiment the amine is selected from: $C_{6-10}$ alkylamine, $C_{6-10}$ alkyldiamine, $C_{6-10}$ alkenylamine, and $C_{6-10}$ alkenyldiamine.

As the skilled person would recognise, the amine either has a single amine functional group ($C_{4-20}$ alkylamine and $C_{4-20}$ alkenylamine) or two amine functional groups ($C_{4-20}$ alkyldiamine and $C_{4-20}$ alkenyldiamine). Furthermore, it would be evident that the amine also either comprises an alkyl chain ($C_{4-20}$ alkylamine and $C_{4-20}$ alkyldiamine) or an alkenyl chain ($C_{4-20}$ alkenylamine and $C_{4-20}$ alkenyldiamine). The present invention benefits from having an amine functional group at an end of the alkyl or alkenyl chain. A terminal amine group has the most electronegative value and the resultant conjugated —H—N site holds the strongest positive charge (about +188.8 Kcal mol$^{-1}$). Therefore, the guest-host interaction between the halide and the amine is the strongest when the amine is at a terminus. The intense electron interaction between a terminal amine group and the halide benefits the electron shuttle efficiency of the present invention.

Accordingly, in certain embodiments, the amine may be selected from: $C_{4-20}$ alkylamine, $C_{4-20}$ alkyldiamine, $C_{4-20}$ alkenylamine, or $C_{4-20}$ alkenyldiamine, wherein an amine functional group is terminal. Although "terminal" within this context would be understood by the skilled person, it refers to having an amine attached to the end of the alkyl or alkenyl chain.

Where there are two amine functional groups within the amine, such as in $C_{4-20}$ alkyldiamine and $C_{4-20}$ alkenyldiamine the two amine groups are preferably at opposing ends of the alkyl or alkenyl chain.

Preferably, the amine is $C_{4-20}$ alkyldiamine and $C_{4-20}$ alkenyldiamine, optionally the two amine groups are at opposing ends of the alkyl or alkenyl chain.

The amine is optionally a $C_{4-20}$ alkyldiamine. Preferably, a $C_{6-12}$ alkyldiamine (optionally, $C_{6-10}$ alkyldiamine) is used as the amine for the present invention. In particularly preferred embodiments the amine is octyldiamine. As discussed above, the amine groups are preferably terminal. Therefore, 1,8-octyldiamine is preferred.

The salt may be formed with exclusively HBr or HI but may also be formed with a mixture of HBr and HI. The mixture may consist of any fraction of HBr and HI, but preferably is in a 1:1 ratio. The compound of the present invention is preferably 1,8-octyldiamine.2HBr, 1,8-octyldiamine.2HI or 1,8-octyldiamine.HBr.HI.

The salt defined above, has excellent properties for a cathode within an energy storage device. Therefore, in an aspect of the invention there is provided a cathode comprising a salt for use as an electrode in an energy storage device, wherein the salt is formed of an acid, selected from HBr, HI or a combination thereof, and an amine, the salt having dissociated bromine ions and/or iodine ions, wherein the amine is a hydrocarbon amine having a hydrocarbon structure that allows for retention of bromine ions and/or iodine ions and allows electron transfer.

In embodiments the cathode may comprise a salt formed of an amine selected from: $C_{4-20}$ alkylamine, $C_{4-20}$ alkyldiamine, $C_{4-20}$ alkenylamine, or $C_{4-20}$ alkenyldiamine; and an acid selected from HBr, HI or a combination thereof.

The salt comprised within the cathode may be defined as set out anywhere in this specification.

The cathode may further comprise an electrical conductor, a binder, and a current collector. Any electrical conductor, binder, or current collector known to the person skilled in the art may be used. However, the electrical conductor is preferably carbon black (optionally carbon black super-P). The binder is preferably polyvinylidene fluoride (PVDF). The current collector is preferably carbon cloth or aluminium foil.

The energy storage device disclosed above may be an electrochemical cell or a battery. Accordingly, in an aspect, the present invention contemplates a battery comprising a salt, wherein the salt is formed of an amine selected from: $C_{4-20}$ alkylamine, $C_{4-20}$ alkyldiamine, $C_{4-20}$ alkenylamine, or $C_{4-20}$ alkenyldiamine; and an acid selected from HBr, HI or a combination thereof.

The salt comprised within the battery may be defined as set out anywhere herein.

The salt of the present invention may be comprised within a cathode of a battery. As such, the battery may further comprise a cathode, comprising the salt of the present invention, an anode, and an electrolyte.

A preferred anode material is zinc. As such, the anode may comprise zinc or be formed of zinc. Preferred electrolyte materials are an aqueous solution of zinc sulphate ($ZnSO_4$).

BRIEF DESCRIPTION OF THE DRAWINGS

Embodiments of the invention are further described by means of example but not in any limitative sense, with reference to the accompanying drawings, in which.

DETAILED DESCRIPTION

The present invention relates to a range of halide organic salts and their use in a cathode of an electrical cell and in batteries. Exemplary salts of the present invention (1,8-octyldiamine.2HBr, 1,8-octyldiamine.2HI or 1,8-octyldiamine HBr.HI) may be represented by the term of ODAX$_1$X$_2$(X represents bromine and/or iodine, ODA denotes protonated 1,8-octanediamine). The salts of the present invention may serve as a cathode matched with a zinc anode. Exemplary batteries of the present invention may be represented as ODAI$_2$//Zn, ODABr$_2$//Zn and ODABrI//Zn in a ZnSO$_4$ electrolyte.

To address issues of prior art halide-based cathodes and batteries comprising such halides, the present invention provides a salt for use as a cathode with highly reliable electrochemical reversibility. The strong host-guest chemisorption interaction with electrons sharing function significantly enhances electrons shuttle efficiency and suppressing polyhalides cross-diffusion. Three customized electrodes based on an identical 1,8-octanediamine (ODA) framework (ODABr$_2$, ODAI$_2$, and ODABrI) exhibit characteristic electrochemical features and redox depth in the aqueous Zn ions system. DFT (Density functional theory) simulation and spectroscopy analysis indicated that the enhanced host-guest interaction is mainly responsible for the superior redox kinetics and cycle durability. In addition to demonstrating the near-theoretical capacities (235 mAh g$^{-1}$ for ODAI$_2$, 312 mAh g$^{-1}$ for ODABr$_2$), the service life (10000 cycles for ODAI$_2$; 3000 cycles for ODABr$_2$) is significantly greater than their elementary counterparts. The present invention has the advantage of facilitating development of high-performance halide-metal batteries with the unexpected advantages of safety, stability, and efficiency.

Figure 1A:
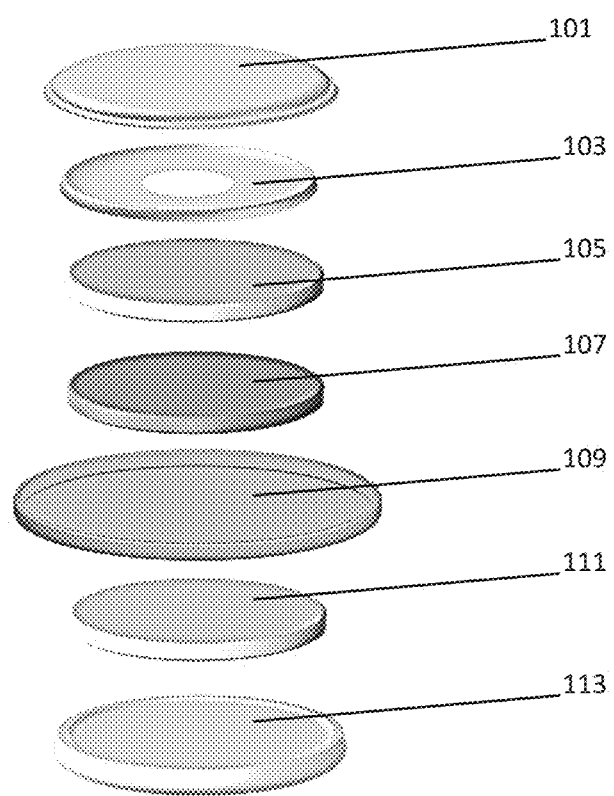
FIG. 1a shows a schematic of a battery produced to test the cathode of the present invention.
Figure 1B:
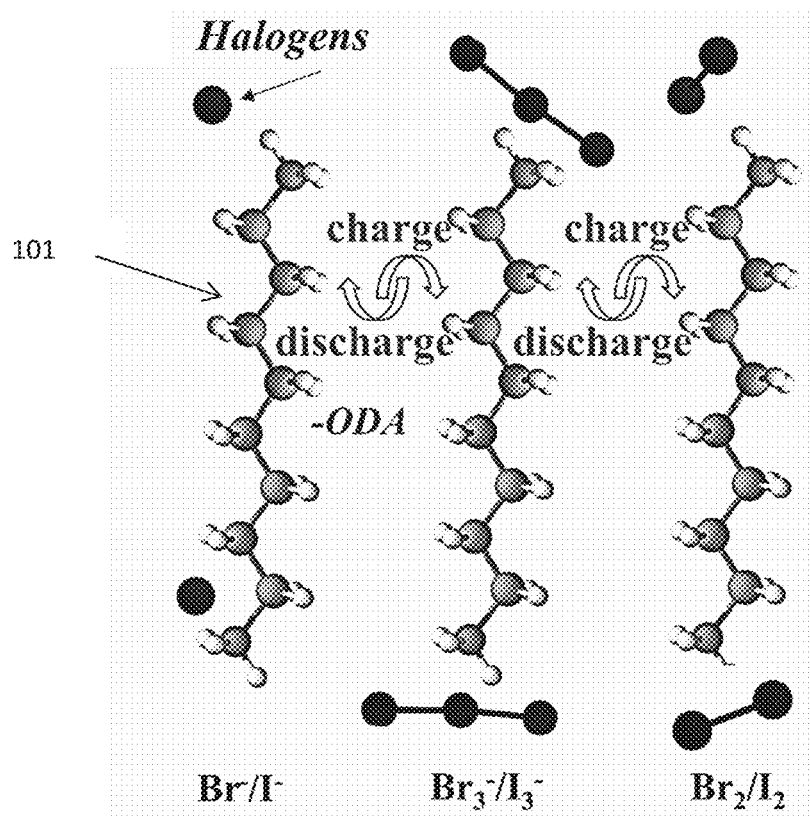
FIG. 1b illustrates the mechanism of the interaction between a halide and an organic molecule according to an embodiment of the invention.

FIG. 1b shows a redox mechanism of a protonated organic halide 101. Upon charging a battery which has in its cathode such an organic halide, the halide anions are bonded at both ends of the protonated organic molecule lose electrons and transform into a higher valence state, ultimately to near zero state, i.e. I$^-$→I$_3^-$→I$_2$ (iodide to polyiodide to iodine) or Br$^-$→Br$_3^-$→Br$_2$ (bromide to polybromide to bromine). At the same time, zinc ions deposited at the zinc anode. In the discharge process, the reverse happens. The zero valence halogens are reversibly reduced to their halide anions, accompanied by a dissolution of the zinc at the anode side. By attraction between the protonated organic chain and the halide species in all the valance states during the redox reaction, the protonated organic chain retains the halide species within the electrode throughout the redox process, i.e. even the negative halide ions at the discharge state, the polyhalides and the elemental matters at the charged state. This is how the electrode is able to mitigate the volatility or escape of the halides.

Figure 1C:
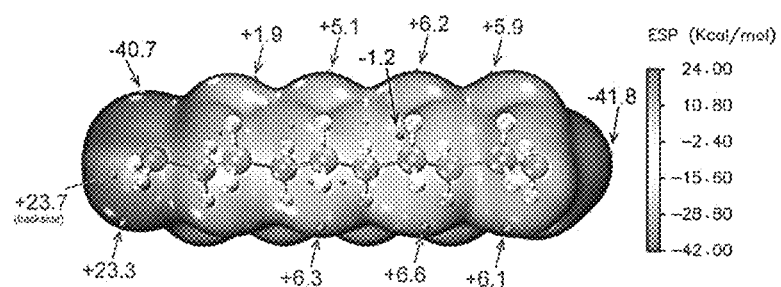
FIG. 1c illustrates the organic molecule of FIG. 1b before protonation.
Figure 1D:
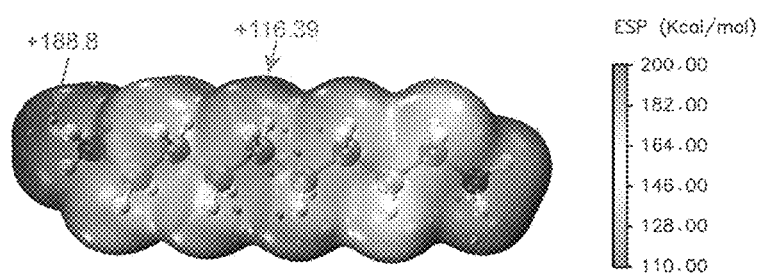
FIG. 1d illustrates the organic molecule of FIG. 1c after protonaton.

FIG. 1c shows the electrostatic potential pattern of 1,8-octanediamine, the two N atoms at both ends being preferable sites for protonation reaction due to their most electronegative values of over −40.7 Kcal mol$^{-1}$. Upon protonation, as shown in FIG. 1d the resultant conjugated —H—N sites hold the strongest positive charge (about +188.8 Kcal mol-1). This charge is capable of binding various halide species because of their most robust polarization interaction.

Both I$^-$ and Br$^-$ will spontaneously form an ionic bond with the —H on N atoms, where the I—H has more electrons transfer and stronger bonding. The intense electron interlaces and share between the protonated host and halogen guest benefit the electrons shuttle and consequent rate capability of the two electrodes in a cell.

DFT simulation and experimental characterizations elucidated that the polar organic chain provided a strong host-guest interaction which allowed for retention of the halide species (I$^-$/Br ions at fully discharged state; I$_3^-$/Br$_3^-$ ions and I$_2$/Br$_2$ at charged state) within the cathode throughout the whole redox reactions. An advantage is that effective immobilization of polyhalides may be achieved, and the undesired shuttle behaviour may be suppressed. Redox kinetics and cycle durability were improved simultaneously. The resultant ODAI$_2$//Zn, ODABr$_2$//Zn, and ODABrI//Zn batteries exhibited the high capacities of 235 mAh g$^{-1}$, 312 mAh g$^{-1}$, and 243 mAh g$^{-1}$ at 0.5 A g$^{-1}$, respectively. Even at a high rate of 4.5 A g$^{-1}$, capacity retention of over 55%, 43%, and 70% may be achieved. In addition, the cycle lifespan of ODAI$_2$//Zn may exceed 10000 times at 4.5 A g$^{-1}$, allowing a capacity attenuation ratio as low as 2% per thousand cycles. For the ODABr$_2$//Zn battery, the capacity attenuation ratio may reach 2.5% per thousand cycles over 3000 cycles at 1 A g$^{-1}$. This result is superior to the reported aqueous elementary counterparts where I$_2$ or Br$_2$ was used as cathode.

EXAMPLES

Synthesis of Salts of the Present Embodiment 1,8-Octanediamine was purchased from a chemical supplier.

To synthesize $ODAI_2$ and $ODABr_2$, 1 mmol of ODA was added into 1 ml HI or HBr solution in a glass vial and stirred at 50° C. for 10 min. Then the solution was slowly cooled down to room temperature with a cooling rate of 2° C. per min. The precipitate was collected and dried in an oven (60° C.) overnight. The mixed halide ODABrI was prepared in a similar way using a mixture of 0.5 ml HBr and 0.5 ml HI.

Cathode Preparation

A cathode of the present invention was prepared by the following procedure. $ODAI_2$, $ODABr_2$, or ODABrI powders, carbon conductor (Super-P), and polyvinylidene fluoride (Aladdin) binder were dispersed into N-methylpyrrolidone solvent with a mass ratio of 7:2:1. The slurry is vigorously stirred for 5 h, and coated onto a carbon cloth surface, followed by drying at 60° C. for 24 h in a vacuum oven.

Battery Preparation

A coin-type 2032 battery was prepared using the following procedure. An exploded view of the battery is shown in FIG. 1a. A Zn disk 107, forming the anode, was pressed against a stainless steel spacer 105. A stainless steel spring 103 is pressed against a smaller cap 101. The spring 103 and smaller cap 101 were pressed against the stainless steel spacer 105 forming a layered system of Zn disk 107, stainless steel spacer 105, stainless steel spring 103 and stainless steel cap 101. A separator 109 was placed against the layered assembly so that it contacted the Zn disk 107. A desired amount of electrolyte was added to the separator 109. A cathode 111 of the present invention, having one or two faces coated by the cathode slurry discussed above, was then placed against the separator 109. If a single side was coated then the coated sides faces the Zn anode 107. The larger cap 113 was then placed on the cathode 111.

The layered system described above was then passed through a press and seal device to form the coin-type battery.

Redox Properties of $ODABr_2$ and $ODAI_2$ Cathodes

Figure 2:
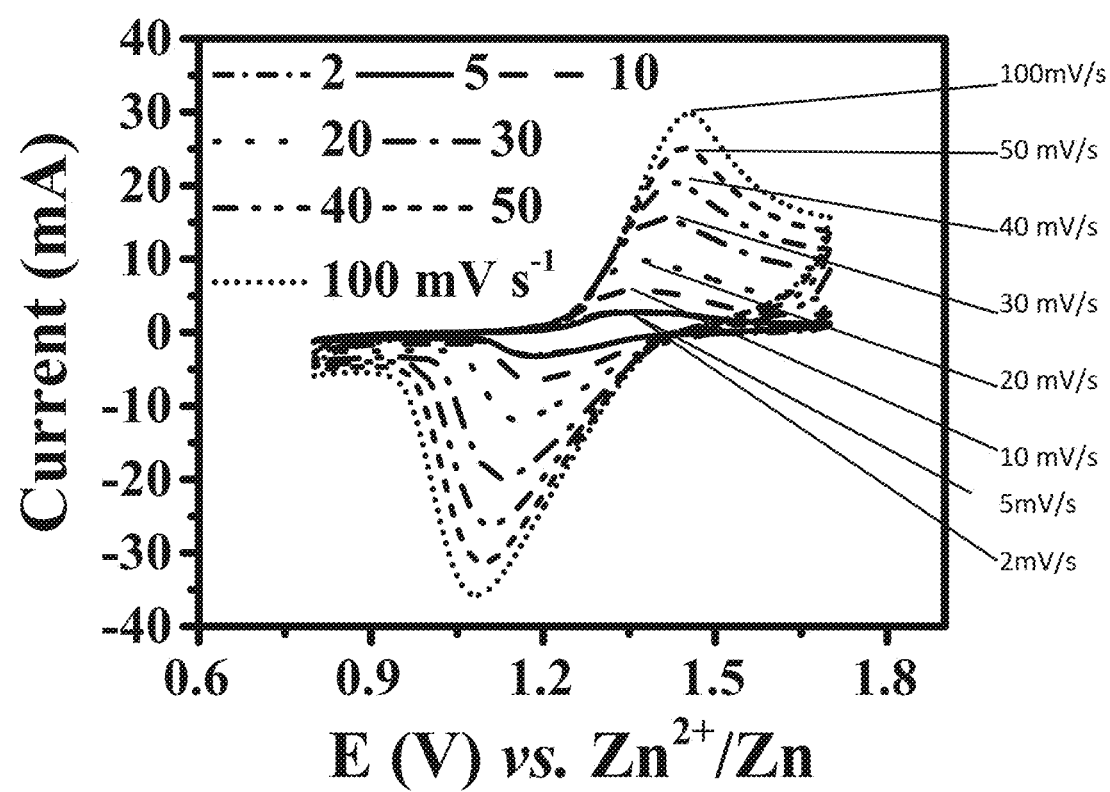
FIG. 2 shows CV curves of ODAI$_2$ cathodes at different sweep rates, ranging from 2 mV s$^{-1}$ to 100 mV s$^{-1}$
Figure 3:
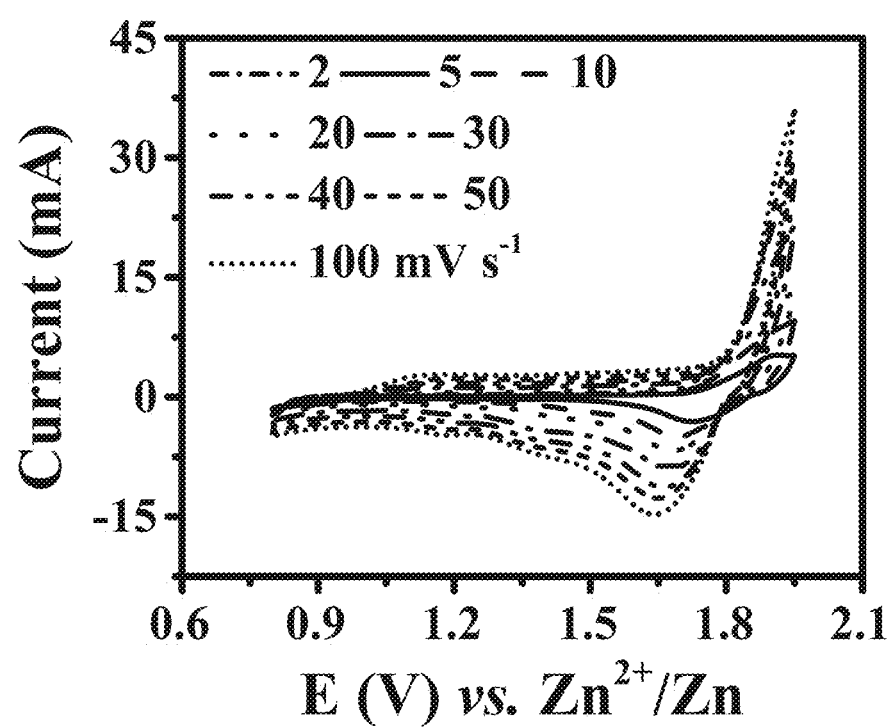
FIG. 3 shows CV curves of ODABr$_2$ cathodes at different sweep rates, ranging from 2 mV s$^{-1}$ to 100 mV s$^{-1}$.
Figure 4:
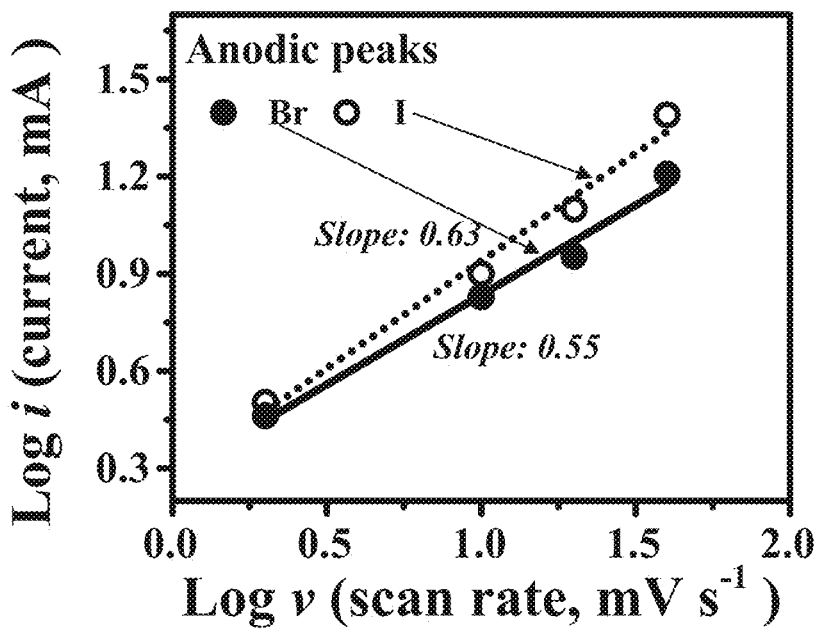
FIG. 4 shows the calculated b values of the two anodic peaks of ODABr$_2$ and ODAI$_2$ cathodes.

The electrochemical properties of the two halide electrodes were explored in an exemplary battery system by employing Zn metal as the anode and 2 M $ZnSO_4$ as the electrolyte. As shown in FIG. 2, over an extensive current range of 2-100 mV $s^{-1}$, the redox peaks of the $ODAI_2$//Zn battery maintain stable, with only a slight deterioration in polarization potential. Even at a high scan rate of 100 mV $s^{-1}$, the anodic potential can still reach up to 1.09 V with a voltage hysteresis of only 0.1 V at 2 mV $s^{-1}$, indicating excellent redox kinetics. Similar trends are also recognized in the $ODABr_2$//Zn battery, in which the voltage hysteresis is estimated within 0.08 V from 1.73 to 1.65 V as the sweep rate rises from 2 to 100 mV $s^{-1}$ (FIG. 3). To elucidate the detailed charge conversion process, the parameter b values of the two reduction peaks were calculated based on the equation below:

$$i=av^b$$

where v represents the sweep rate, and i stands for the response current. The b value should be distributed in the range of 0.5-1. When b is equal to 0.5, the electrochemical process is solely dominated by the diffusion-controlled behaviour; while when the b value is equal to 1, the capacitive contribution ultimately prevails. As shown in FIG. 4, the calculated b values of $ODAI_2$//Zn and $ODABr_2$//Zn batteries were 0.55 and 0.63, respectively, recognizing that the conversion reactions are synergistically controlled by the two above mechanisms with the diffusion-controlled behaviour dominating.

Figure 5:
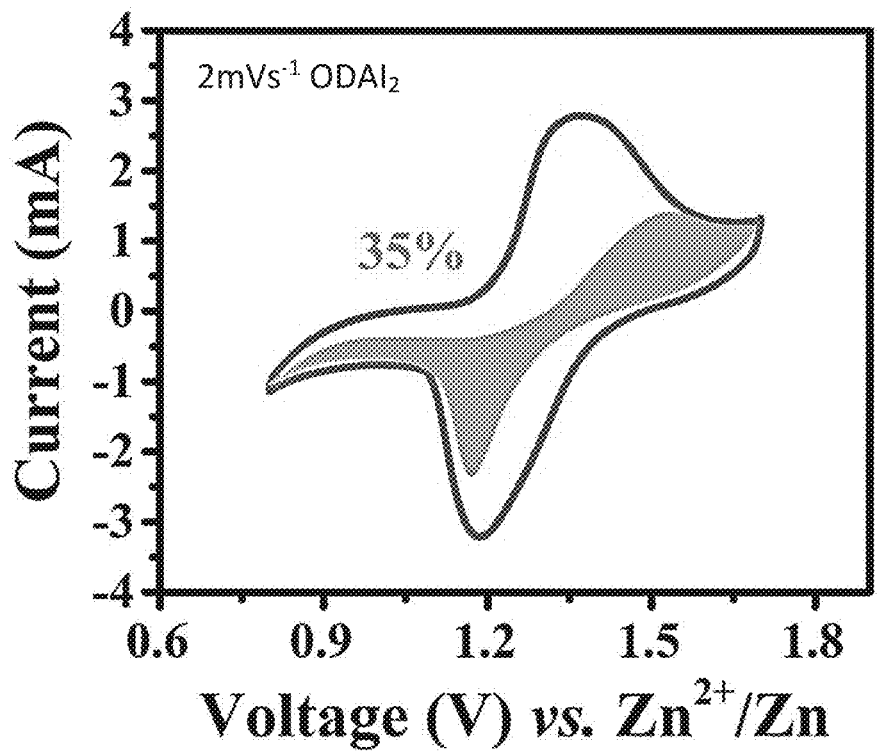
FIG. 5 shows an illustration of the calculated capacitive and diffusion-controlled contributions of ODAI$_2$ cathode at 2 mV s$^{-1}$.
Figure 6:
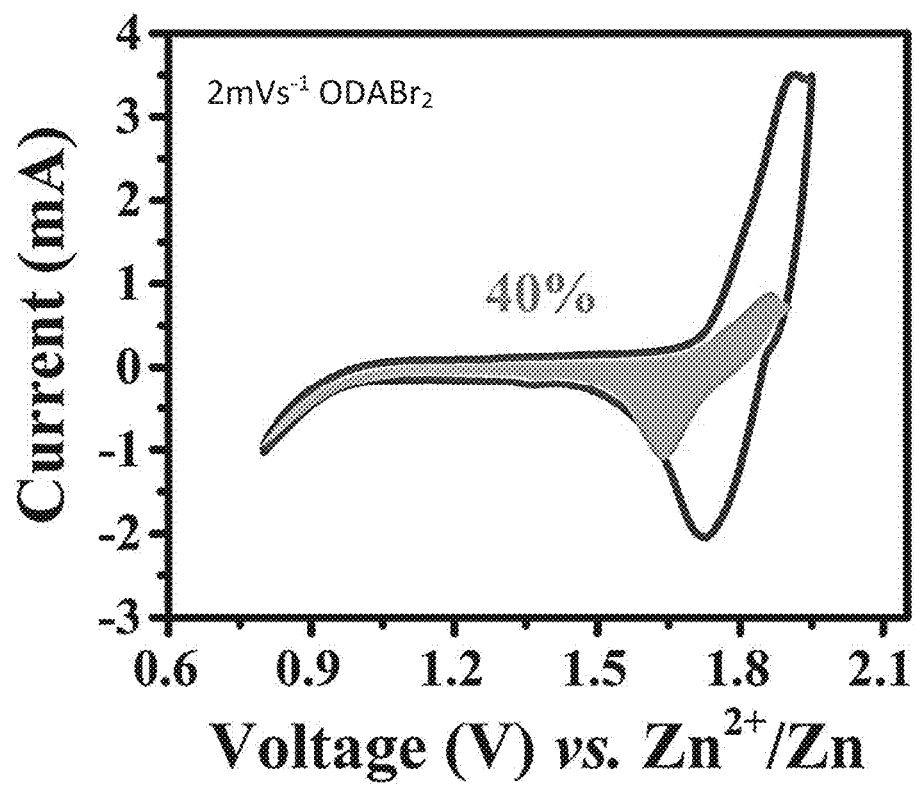
FIG. 6 shows The illustration of the calculated capacitive and diffusion-controlled contributions of ODABr$_2$ cathode at 2 mV s$^{-1}$.
Figure 7:
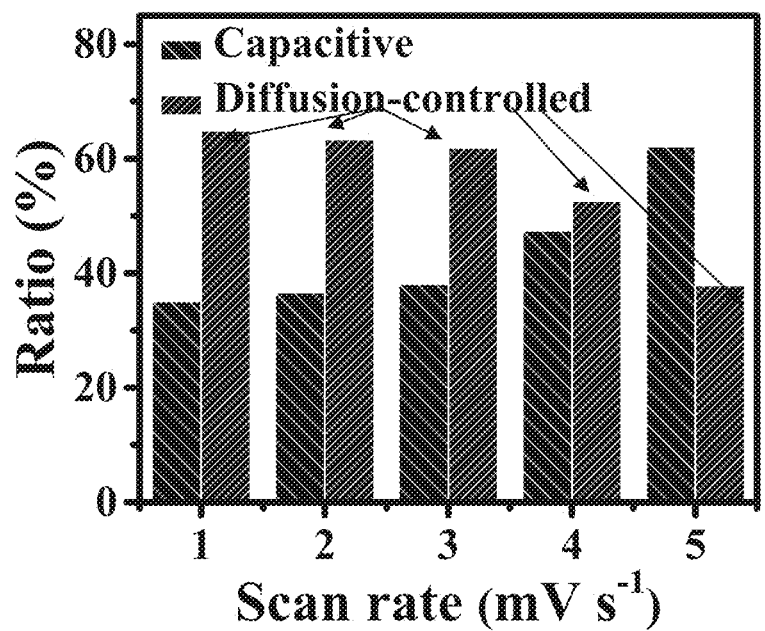
FIG. 7 shows The calculated capacitive and diffusion-controlled contribution of ODAI$_2$ cathode at different scan rates.
Figure 8:
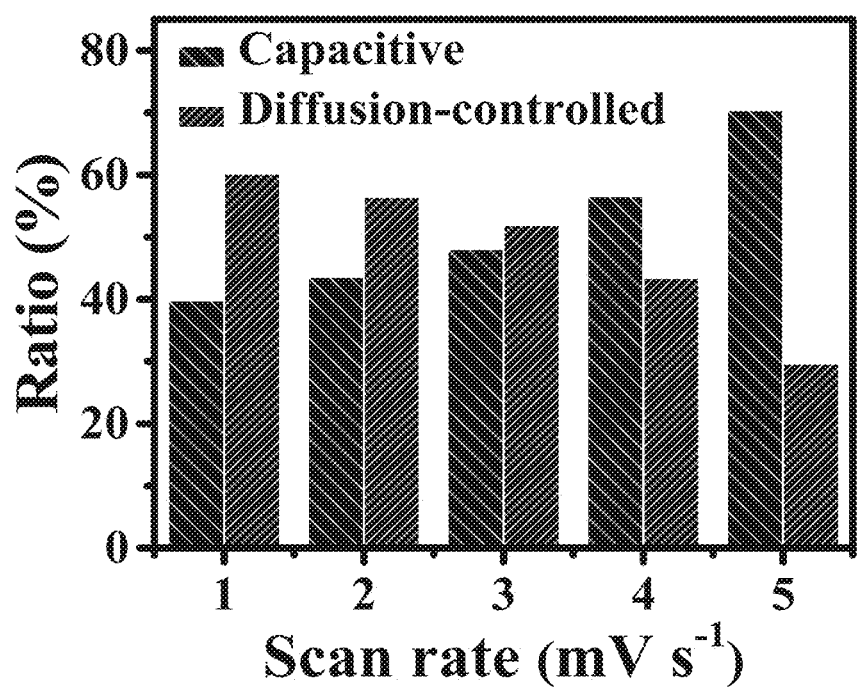
FIG. 8 shows The calculated capacitive and diffusion-controlled contribution of ODABr$_2$ cathode at different scan rates.

Furthermore, a more sophisticated quantitative contribution analysis was calculated based on the equation below:

$$i(V)=k_1v+k_2v^{1/2}$$

where i represents response current, v represents the sweep rate, $k_1v$ represents the capacitive contribution part, and $k_2v^{1/2}$ represents the diffusion-controlled contribution part. At 2 mV $s^{-1}$, the capacitive part and diffusion-controlled part account for 35% and 65% respectively in $ODAI_2$//Zn battery (FIG. 5), while these values are 40% and 60% in $ODABr_2$//Zn battery (FIG. 6). As the scan accelerates, the capacitive contribution increased from 35% at 2 mV $s^{-1}$ to 62% at 40 mV $s^{-1}$ in $ODAI_2$//Zn battery, while that of $ODABr_2$//Zn battery are located at 40% at 2 mV $s^{-1}$ and 71% at 40 mV $s^{-1}$, as summarized in FIGS. 7 and 8.

Electrochemical Performance of $ODABr_2$//Zn and $ODAI_2$//Zn Batteries

Figure 9:
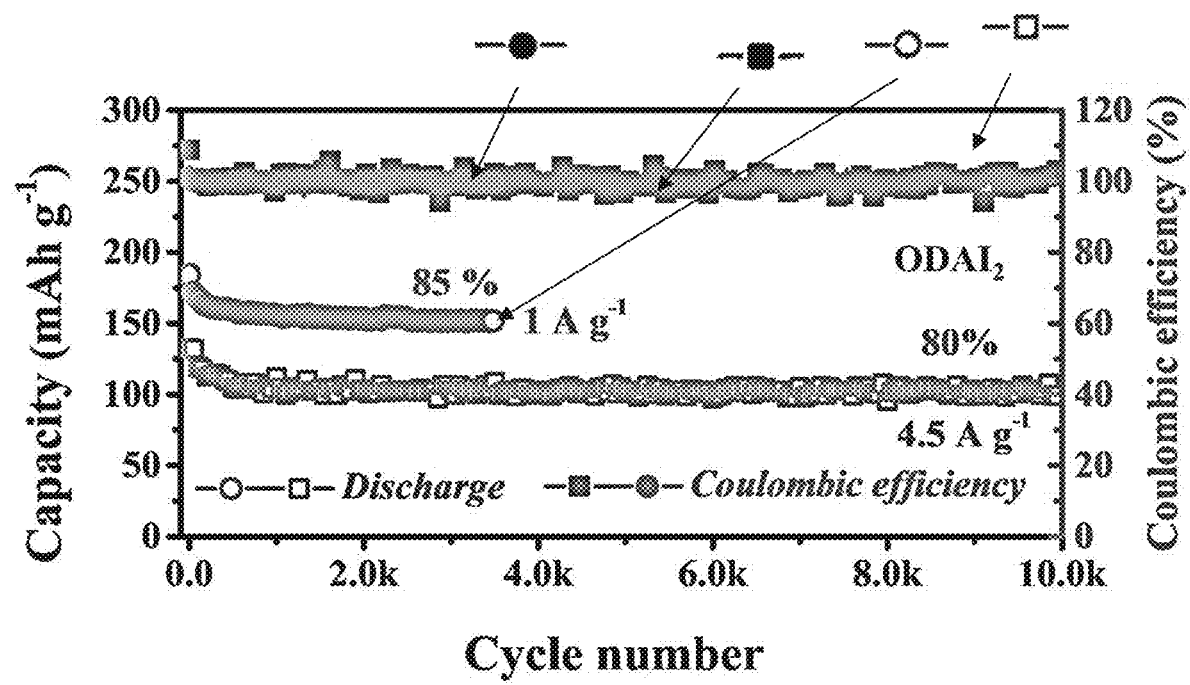
FIG. 9 shows prolonged cyclic performance of ODABr$_2$//Zn battery at 1 A g$^{-1}$.

After contemplating the redox activity of the two electrodes, the electrochemical performance was further investigated involving rate capability and cyclic durability. As discussed above, the persistent shuttle behaviour of elemental halide cathodes presented a significant impairment to the service life of the battery since the active halogen species were lost from the cathode as charging and discharging cycles continued. The salt of the present invention provides the benefit of a significantly improved capacity retention, as shown with a prolonged cycle test. For the $ODAI_2$ cathode, the assembled $ODAI_2$//Zn battery suffers from only 15% capacity fade after 3500 cycles at a low current density of 1 A $g^{-1}$ (FIG. 9).

Moreover, when the current density was increased to 4.5 A $g^{-1}$, the lifespan can be significantly extended to 10,000 cycles with a low capacity decay of about 20%, delivering an outstanding decay ratio of 2% per thousand cycles. Such cyclic durability outperforms conventional $I_2$ cathodes.

Figure 10:
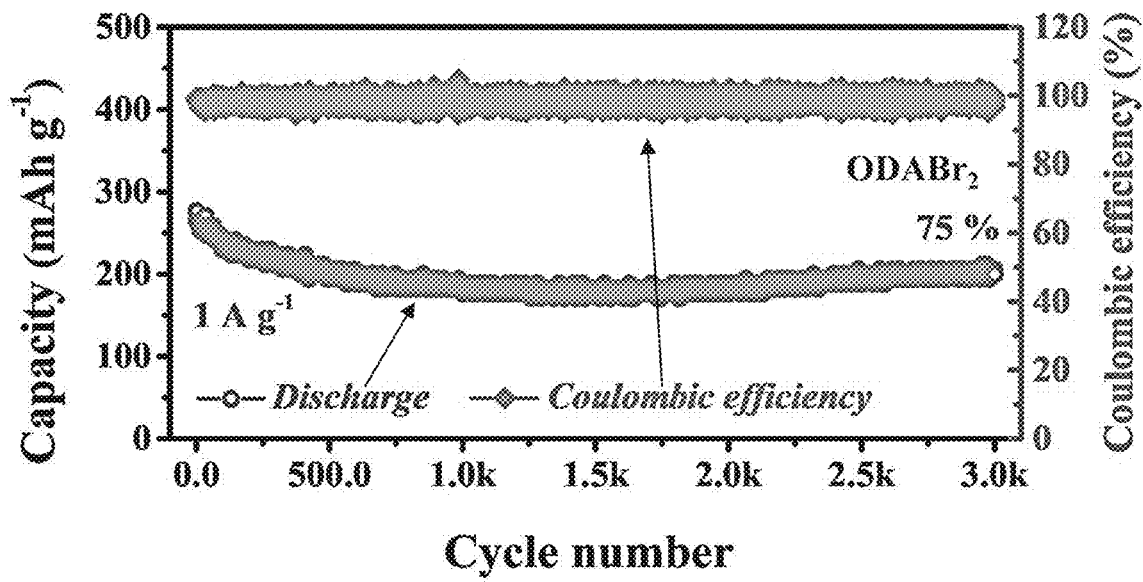
FIG. 10 shows prolonged cyclic performance of ODAI$_2$//Zn battery at 1 A g$^{-1}$ and 5 A g$^{-1}$

Similarly, the discharge capacity retention of $ODABr_2$/Zn battery can remain up to 75% after over 3000 cycles at 1 A $g^{-1}$, indicating a capacity decay ratio of below 2.5% per thousand cycles, superior to that of reported $Br_2$ elementary counterparts (FIG. 10).

Figure 11:
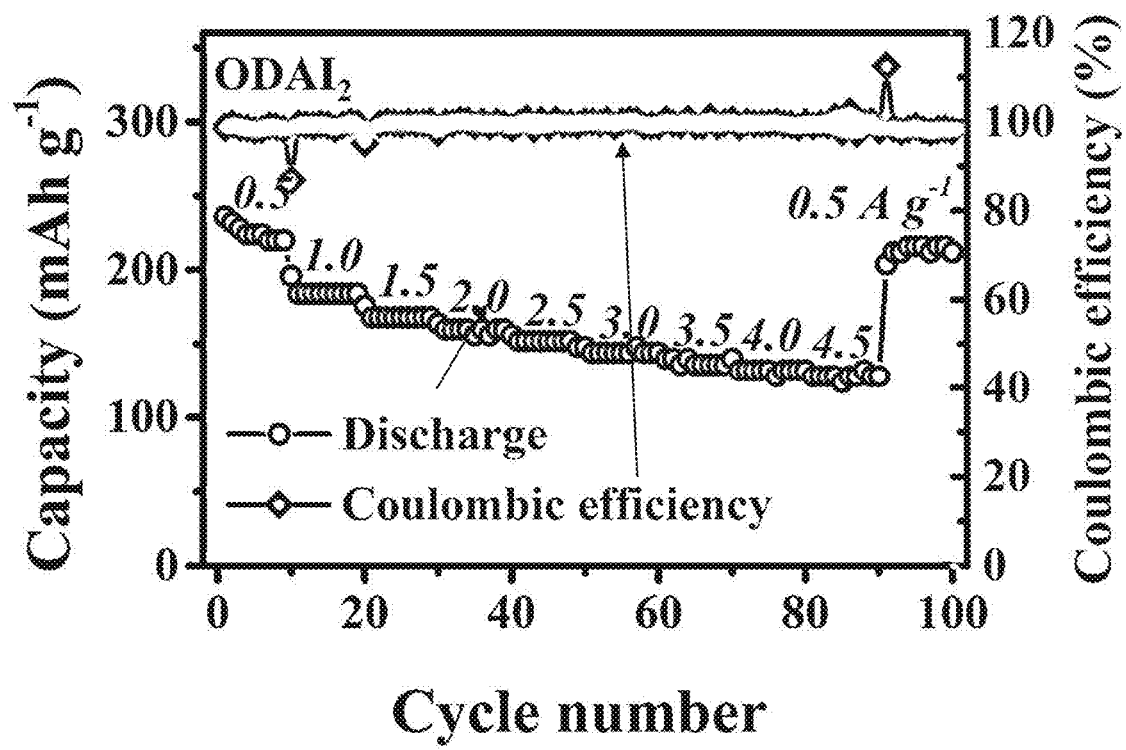
FIG. 11 shows rate capability of ODABr$_2$//Zn battery in the range of 0.5-4.5 A g$^{-1}$.

The rate capability was tested at a wide current range of 0.5-4.5 A $g^{-1}$. The results of this test are shown in FIG. 11.

Figure 12:
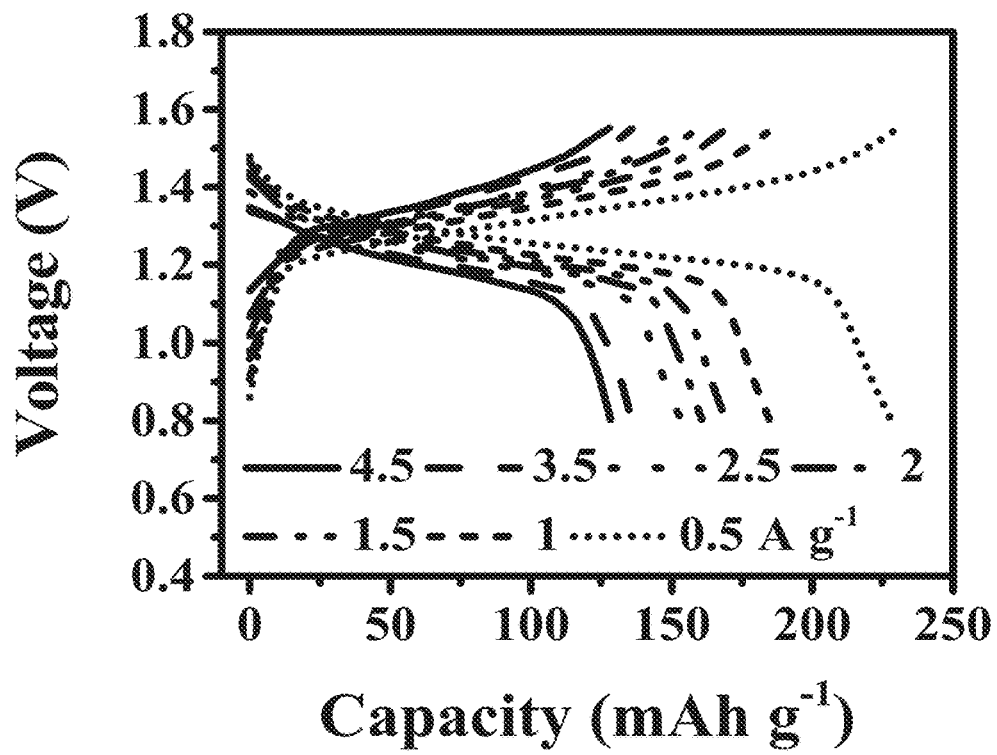
FIG. 12 shows the GCD curves of ODABr$_2$//Zn battery.

The $ODAI_2$//Zn battery of this invention is capable of delivering a reversible capacity of over 235 mAh $g^{-1}$ at 0.5 A $g^{-1}$. This is close to the theoretical upper limit of the $I^-/I_2$ redox couple. When the applied rate was increased to 4.5 A $g^{-1}$, the capacity was still found to be up to 129 mAh $g^{-1}$, showing an excellent capacity retention of 55%. When the current is reset back to 0.5 A $g^{-1}$, the capacity can be restored to 218 mAh $g^{-1}$. The corresponding galvanostatic charge-discharge (GCD) curves of the rate capability are given in FIG. 12, exhibiting apparent discharge/charge plateaus in all cases. The discharge voltage polarization was estimated to be 0.6 V, declining from 1.26 V to 1.20 V as the current increased by a factor of nine, suggesting superior redox kinetics.

Figure 13:
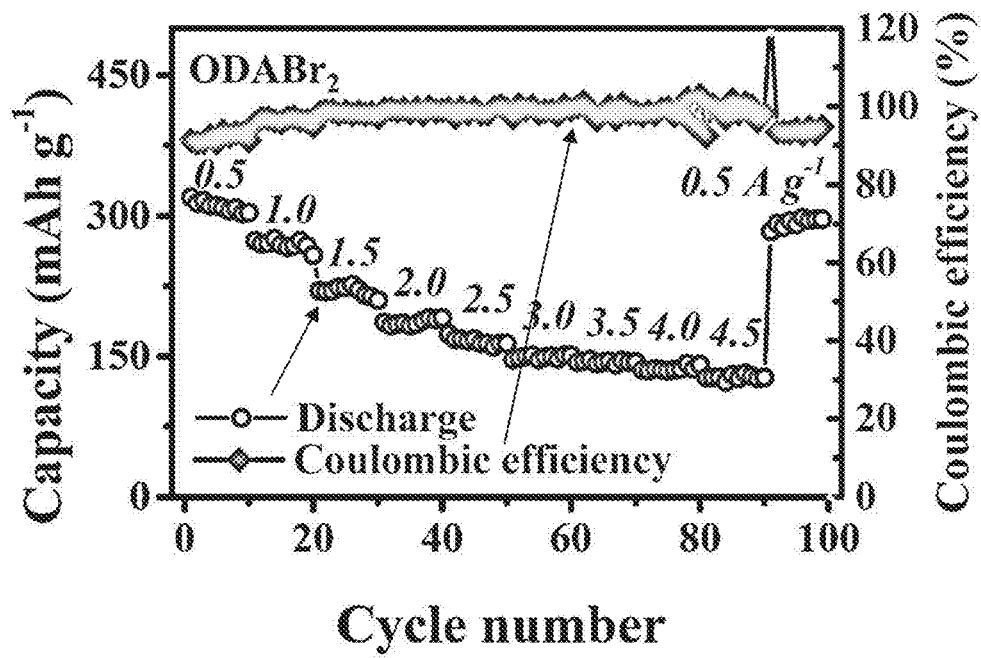
FIG. 13 shows the rate capability of ODABr$_2$//Zn battery in the range of 0.5-4.5 A g$^{-1}$.
Figure 14:
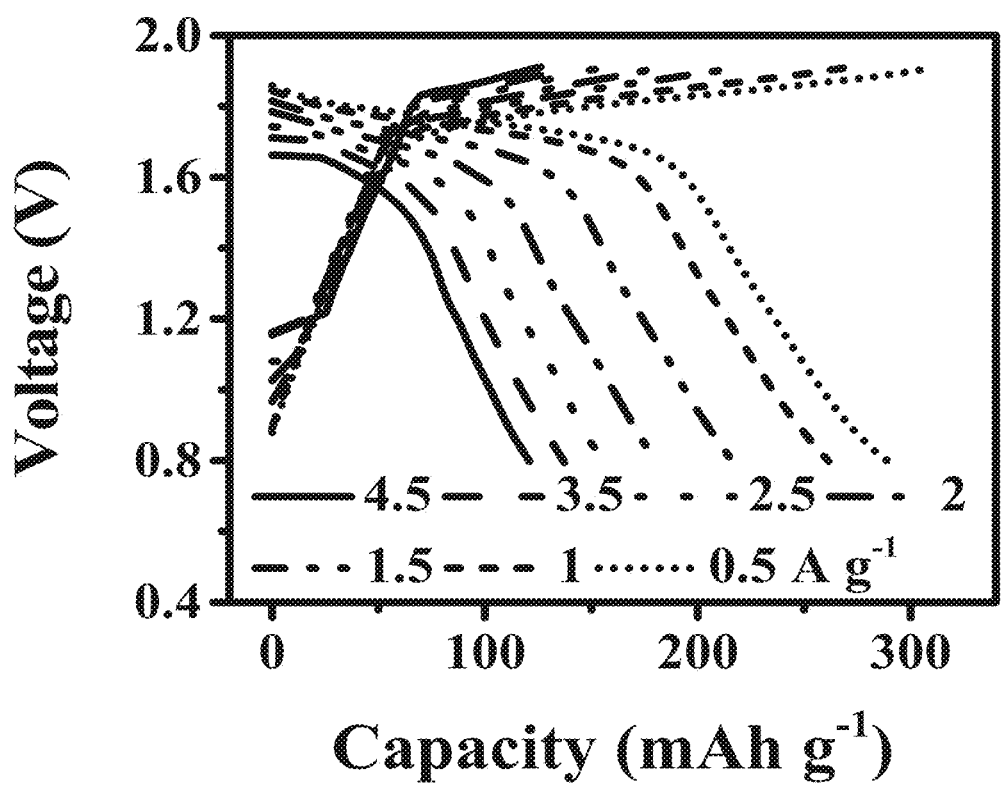
FIG. 14 shows the corresponding GCD curves of ODABr$_2$//Zn battery.

Similarly, exceptional kinetics are also detected in the $ODABr_2$ cathode. As shown in FIG. 13, the $ODABr_2$//Zn battery displays a high capacity of up to 312 mAh $g^{-1}$ at 0.5 A $g^{-1}$, and remained at 133 mAh $g^{-1}$ at a harsh rate of 4.5 A $g^{-1}$. More unexpectedly, a distinct and high discharge voltage plateau was observed at 1.80 V, matching the CV results well (FIG. 14). As the current sharply increased, the plateau remained intact despite capacity suffering from continuous fading. Such high redox potential, close to the theoretical upper limit, may be inextricably linked to the strong host-guest interaction because of the resultant efficient electron transfer of the salt of the present invention.

Figure 15:
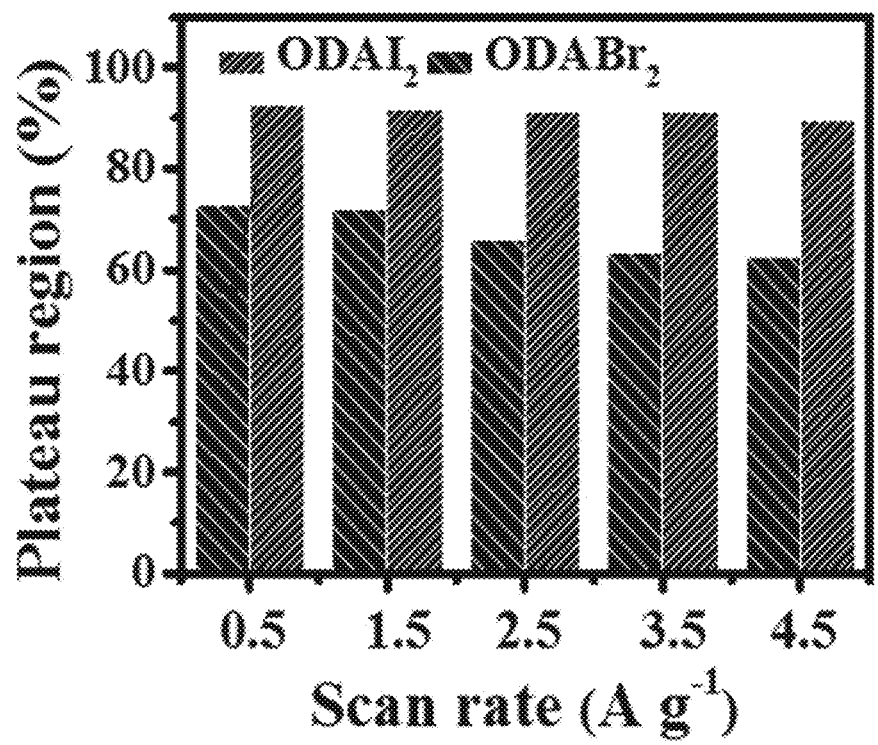
FIG. 15 shows calculated contributions of the plateau regions to energy output at different rates.

An unexpected advantage worth mentioning that the two organic halide electrodes have achieved the ultra-flat voltage plateaus and satisfactory plateau region ratios of conversion-type batteries. To further clarify their practical superiority, the specific contributions of the discharge plateau to capacity and energy density were determined. As shown in FIG. 15, at a low rate of 0.5 A g$^{-1}$, over 65% and 91% of the total capacity was obtained from the plateau regions in ODABr$_2$//Zn battery and ODAI$_2$//Zn battery, respectively. More significantly, these values can reach up to 72.8 and 92.3% in terms of energy density, indicating their promising output potential in the high-voltage region. Benefiting from the high reversibility and fast kinetics, the contribution fractions to energy density were above 67% and 80% at a high rate of 4.5 A g$^{-1}$.

Figure 16:
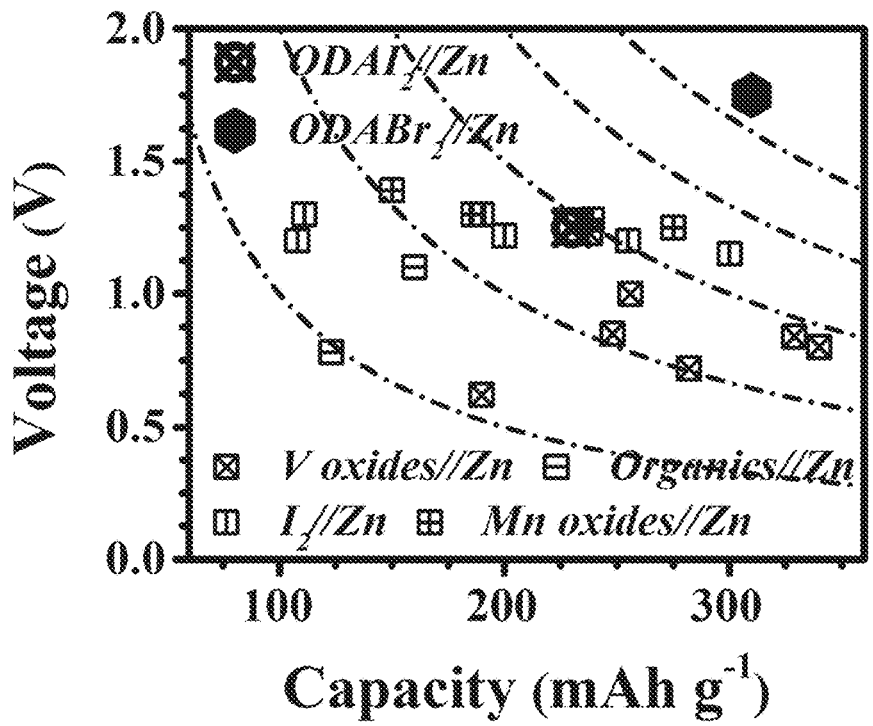
FIG. 16 shows Comparison of capacity vs. average voltage of the present invention to reported aqueous batteries, including I$_2$-metal, Mn oxides//Zn, and V oxides//Zn, organics//Zn systems.

To demonstrate the electrochemical superiority of the two new cathodes in an aqueous Zn batteries, batteries of the present invention (ODAI$_2$//Zn and ODABr$_2$//Zn batteries), were compared with previously reported cathodes in terms of average voltage, capacity, and energy density. As summarized in FIG. 16, Mn-oxides, V-oxides, organics, and elemental I$_2$ cathodes were all investigated. For instance, Mn-oxides stood out at relatively high voltage (1.0-1.6 V) but were limited by output capacity (150-280 mAh g$^{-1}$), while vanadium oxides behaved the opposite way with low voltage and high capacity (0.4-1.1 V; 180-350 mAh g$^{-1}$). Intercalation/extraction-type organic cathodes performed slightly worse than the two (0.7-1.2 V; 110-180 mAh g$^{-1}$). Surprisingly, the energy density of the ODABr$_2$//Zn battery reaches up to 524 Wh kg$^{-1}$, benefiting from the completely reversible conversion of the bonded halogens. As such, the ODAI$_2$//Zn and ODABr$_2$//Zn batteries were distinctly competitive, especially the ODABr$_2$//Zn system. Against the traditional elemental halide counterparts, the present invention provides an improvement in terms of stability and safety without sacrificing the electrochemical activities.

Redox Mechanism Analysis

The present invention takes advantage of the reversible redox of I$^-$/I$_2$ and Br/Br$_2$ couples and complete electron transfer. Upon charging, the I$^-$/Br anions bonded at both ends of the organic chain loses electrons and transform to a high valence state and ultimately near-zero valence state (I$_2$/Br$_2$), while Zn ion deposition occurs at the Zn anode side. In the opposite discharge process, the zero-valence halogens are reversibly reduced to their corresponding I$^-$/Br anions, accompanied by a Zn dissolution process in the Zn anode side. Distinctly differing from the traditional elemental halide cathodes, the protonated organic chain can naturally impose a profound restraint on the halide species throughout the entire redox process, covering the negative halide ions at the discharged state, polyhalides and elemental matters at the charged state.

Figure 17:
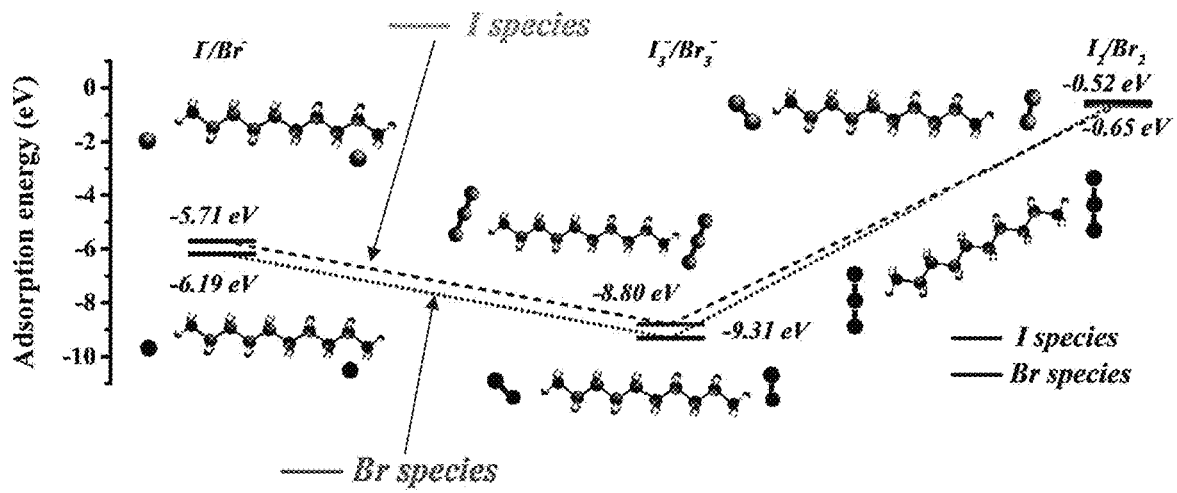
FIG. 17 shows the calculated adsorption energy of protonated ODA host to various halide species (I$_2$/Br$_2$; I$^-$/Br$^-$; Br$_3^-$/I$_3^-$).

A quantitative analysis in the host guest interaction between the halide ions and the protonated ODA was performed. As shown in FIG. 17, for all halides species covering anions and elemental types, the ODA host displays exceptional adsorption energies: −5.71 eV of I$^-$, −8.80 eV of I$_3^-$, −0.65 of I$_2$, −6.19 eV of Br, −9.31 eV of Br$_3^-$, −0.52 eV of Br$_2$, which is far superior to that of traditional hosts. Accordingly, this desired host-guest interaction force, may play an important role in inhibiting the undesired shuttle behaviour of polyhalides, and hence remarkably contributes to the cyclic durability.

The Hybrid ODABrI Cathode

Figure 18:
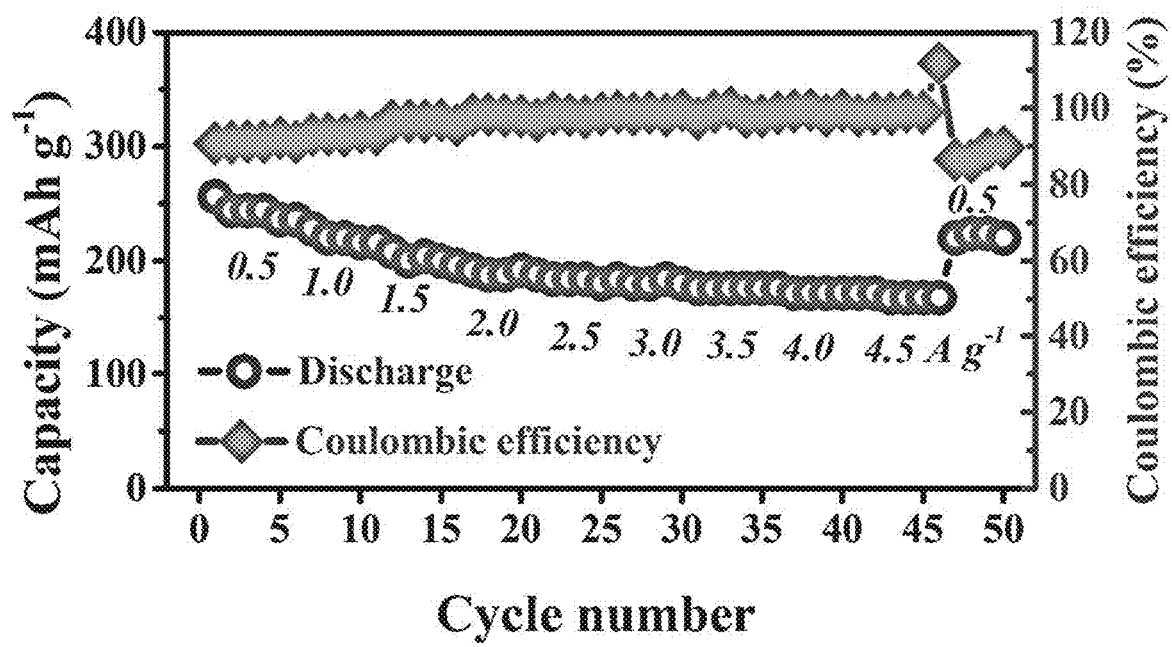
FIG. 18 shows the rate capability of ODABrI//Zn battery in the range of 0.5-4.5 A g$^{-1}$.
Figure 19:
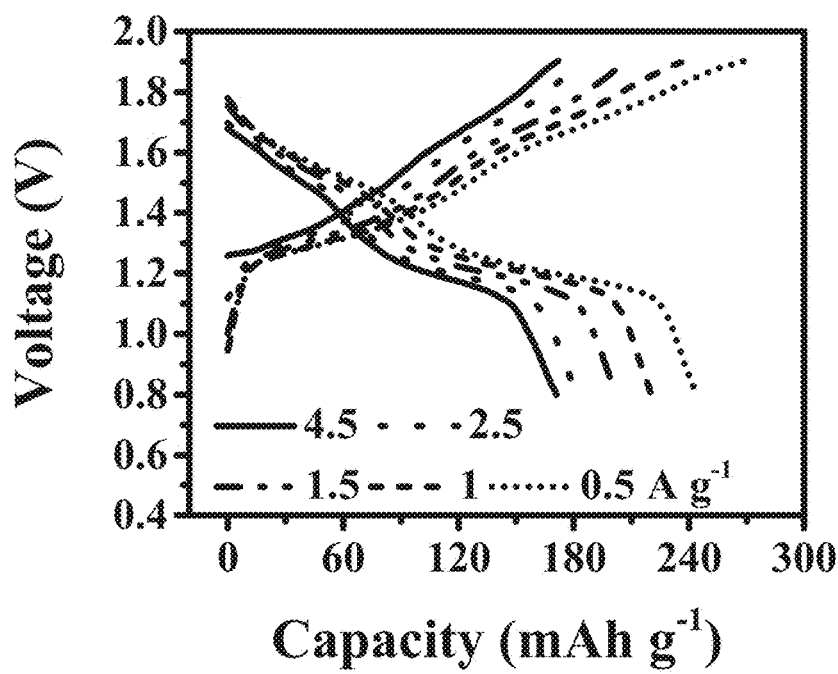
FIG. 19 shows the corresponding GCD curves of ODABrI//Zn battery.
Figure 20:
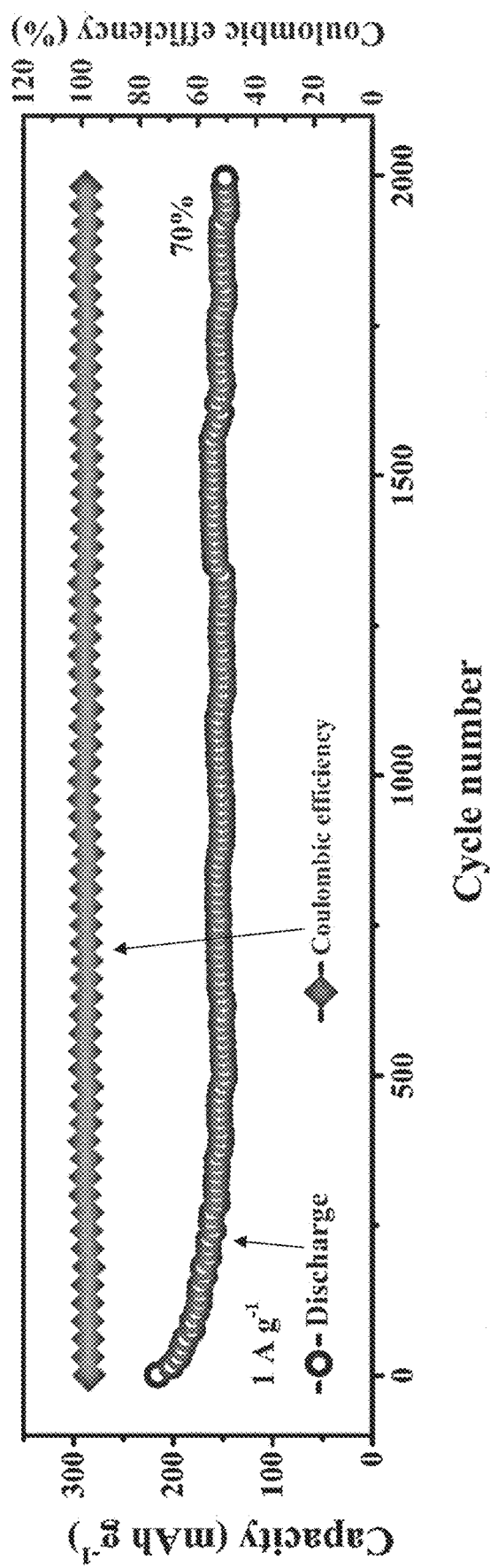
FIG. 20 shows prolonged cyclic performance of ODABrI//Zn battery at 1 A g$^{-1}$.

Fast redox kinetics is believed to trigger the current insensitivity and superior rate capability. As seen in the rate test in FIG. 18, the ODABrI//Zn battery delivered the specific capacities of 243, 220, 202, 188, 184, 181, 177, 170 mAh g$^{-1}$ at 0.5, 1.0, 1.5, 2.0, 2.5, 3.0, 3.5, 4.0 A g$^{-1}$, respectively. Remarkably, a considerable capacity of 168 mAh g$^{-1}$ can be attained even at the high current density of 4.5 A g$^{-1}$, accounting for the capacity retention of 70%, which is even superior to the identical halide counterparts. Meanwhile, the corresponding GCD curves are displayed in FIG. 19, showing two pairs of well-defined discharging/charging plateaus as expected at all rates, in good agreement with the above CV results. Two discharge plateaus can always be retained intact without any detectable fluctuation despite a dramatically nine-fold change in scan rates. Also, the consequent two voltage hysteresis was estimated to be within 0.04 V for I redox and 0.06 V for Br redox, indicating their exceptional kinetics. This demonstrates that the superior host-guest interaction derived from the protonated organic chain is also achieved by this hybrid ODABrI cathode. Furthermore, regarding the long-term cycling test at 1 A g$^{-1}$, the capacity fade was limited within 30% over 2000 cycles, indicating a low decay ratio of 3% per thousand cycles (FIG. 20). The introduced strong chemisorption interaction may still function and may be majorly responsible for such excellent cycle durability in complicated halide conditions.

CONCLUSION

The salts of the present invention have the advantage of providing strong host-guest chemisorption interaction and electron sharing function. This has significant importance to trigger the efficient electron transfer and inhibit the cross-diffusion of the polyhalide species generated during the charging and discharging process. In addition to eliminating the safety hazards, both redox kinetics and cycle durability are significantly enhanced with the salts of the present invention.

A further advantage is that, batteries of the present invention can achieve capacities close to the theoretical limit of a zinc/halide cell. Capacities of 235 mAh g$^{-1}$ are achieved in the ODAI$_2$//Zn and a capacity of 312 mAh g$^{-1}$ are achieved in the ODABr$_2$//Zn batteries at 0.5 A g$^{-1}$. Moreover, the resultant energy density of 524 Wh kg$^{-1}$ is achieved in the ODABr$_2$//Zn battery, superior to most reported aqueous zinc batteries.

While there has been described in the foregoing description preferred embodiments of the present invention, it will be understood by those skilled in the technology concerned that many variations or modifications in details of design, construction or operation may be made without departing from the scope of the present invention as claimed.

The skilled reader would obtain guidance by this teaching to look for organic molecules that are capable of binding to the difference valence states of halides, or any other ionic compounds, ions and atoms suitable for use in cathodes. The organic molecules will have a molecular weight and stearic properties suitable for retaining the halides from vaporising or leaking away.

The invention claimed is:

1. A battery comprising:
a cathode consisting essentially of an electric conductor, a binder, and a salt selected from the group consisting of 1,8-octyldiamine.2HBr, 1,8-octyldiamine.2HI, and 1,8-octyldiamine.HBr.HI; and
an anode formed from a zinc metal.

2. A method for producing a cathode of a zinc-halide battery comprising:
dispersing a salt, an electric conductor, and a binder in a mass ratio of 7:2:1 in a solvent thereby forming a slurry;
applying the slurry on a substrate; and
drying the slurry coated substrate at 60° C. for 24 hours in a vacuum oven thereby producing the cathode, wherein, the salt is selected from the group consisting of 1,8-octyldiamine.2HBr, 1,8-octyldiamine.2HI, and 1,8-octyldiamine.HBr.HI, wherein, the battery comprising the cathode consisting essentially of the electric conductor, the binder, and the salt and an anode formed from a zinc metal.

3. The method of claim 2, wherein the electric conductor is carbon, the binder is polyvinylidene fluoride, the solvent is N-methylpyrrolidone, and the substrate is a carbon cloth.

* * * * *